United States Patent [19]

Choksi et al.

[11] Patent Number: 5,076,322

[45] Date of Patent: Dec. 31, 1991

[54] VACUUM LIMITING, REGULATING DEVICE

[76] Inventors: Pradip Choksi; Rekha P. Choksi, both of 19035 Yolanda Ave., Northridge, Calif. 91326

[21] Appl. No.: 597,185

[22] Filed: Oct. 15, 1990

[51] Int. Cl.$^5$ .......................................... G05D 16/02
[52] U.S. Cl. ........................ 137/505.13; 137/505.38; 137/510; 137/907
[58] Field of Search ............... 137/510, 907, 859, 114, 137/505.13, 505.38

[56] References Cited

U.S. PATENT DOCUMENTS

| | | | |
|---|---|---|---|
| 2,394,911 | 2/1946 | Griswold | 137/859 X |
| 3,144,044 | 8/1964 | Anthes | 137/510 X |
| 3,469,582 | 9/1969 | Jackson | 137/510 X |
| 4,044,735 | 8/1977 | Sumiyoshi | 137/907 X |
| 4,416,307 | 11/1983 | Detweiler | 137/907 X |
| 4,592,385 | 6/1986 | Semon | 137/907 X |

FOREIGN PATENT DOCUMENTS 957118 5/1964 United Kingdom ................ 137/907

*Primary Examiner*—Stephen M. Hepperle
*Attorney, Agent, or Firm*—William W. Haefliger

[57] ABSTRACT

A device for limiting the applied vacuum in a fluid suctioning system comprising a chamber having an inlet at which a suction level or levels $V_x$ is or are to be maintained, and an outlet to which vacuum level $V_2$ is applied, wherein $V_x < V_2$, fluid being sucked through the shapes via the inlet and outlet; an annular seat in the chamber, the chamber containing an upstream flow zone $R_1$ between the inlet and the seat, and a downstream flow zone $R_2$ between the seat and the outlet; and a diaphragm at the upstream side of the seat and extending crosswise thereof and crosswise of at least a portion of the zone $R_1$; the diaphragm carried for movement toward the seat when the vacuum level in $R_1$ rises to a predetermined level, to reduce or block fluid flow through the chamber, the diaphragm movable away from the seat when the vacuum level in $R_1$ falls below a predetermined level.

17 Claims, 2 Drawing Sheets

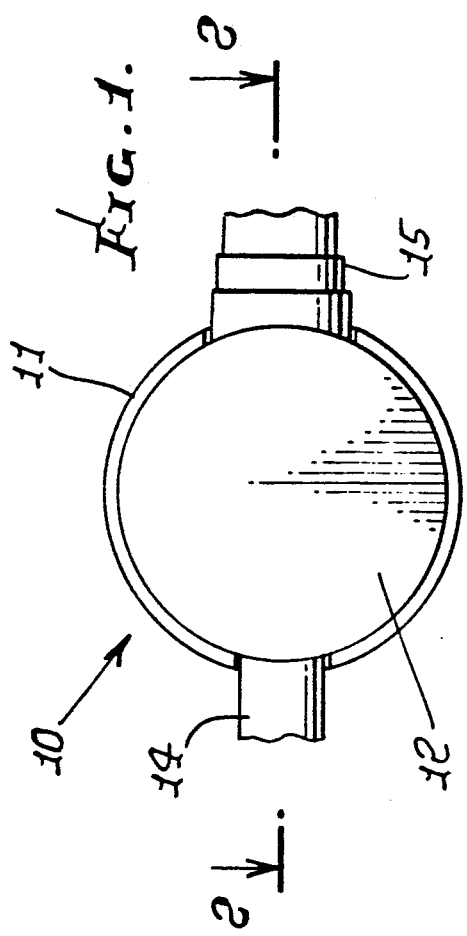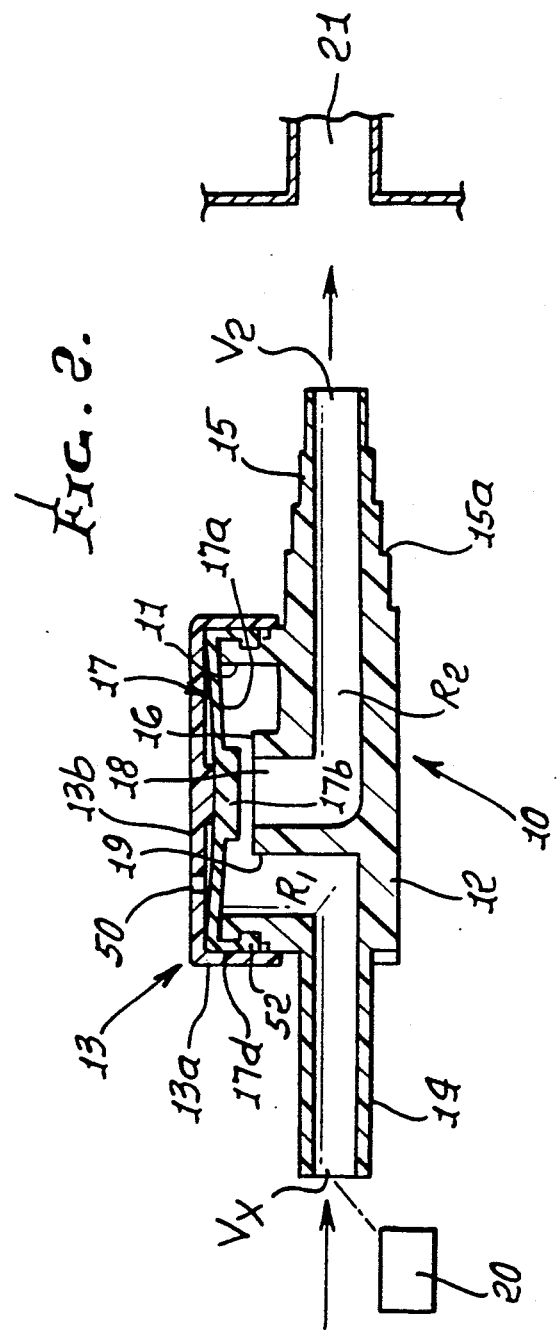

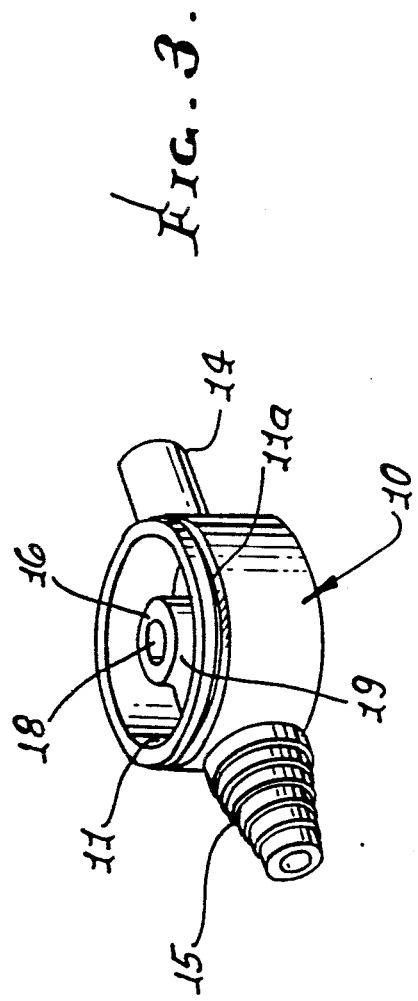
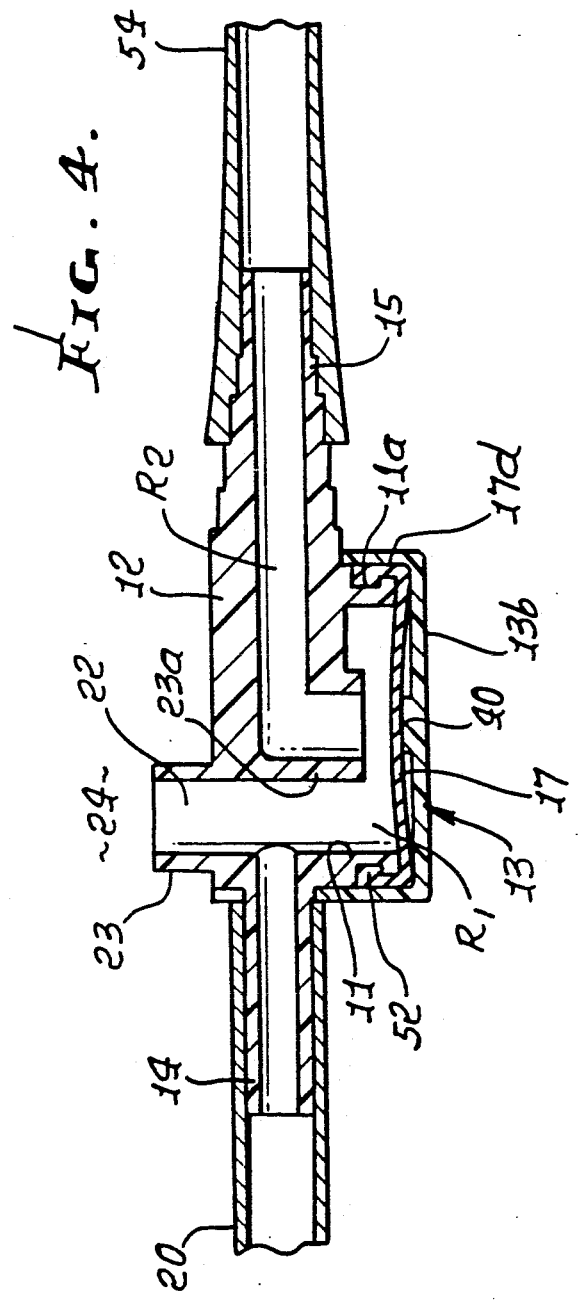

5,076,322

VACUUM LIMITING, REGULATING DEVICE

BACKGROUND OF THE INVENTION

This invention relates generally to vacuum suctioning of fluids, as during clinical procedures; and more specifically concerns very simple vacuum limiting or regulating apparatus.

In the hospital, vacuum is used for suctioning fluids during several clinical procedures. Two examples of these procedures are suctioning of mucus from the trachea and bronchi, and drainage of blood and other fluids from wound sites after surgery.

During these procedures, it is important to limit the suction to a value of 120 mm Hg to minimize trauma to the mucosa and surrounding blood vessels. This is usually done with a vacuum regulator. These regulators are expensive instruments that require regular maintenance. In hospitals these devices are quite often not available in every room where the suctioning procedure is to be carried out. Also, many instruments are found to be malfunctioning.

In view of the above, need exists for a low cost disposable device that would limit the value o vacuum to a pre-set level.

SUMMARY OF THE INVENTION

It is a major object of the invention to provide simple, efficient apparatus meeting the above need. Basically, the apparatus of the invention comprises a device for limiting the applied vacuum in a fluid suctioning system, and includes (a) a chamber having an inlet at which a suction level or levels $V_x$ is or are to be maintained, and an outlet to which vacuum level $V_2$ is applied, wherein $V_x < V_2$, fluid being sucked through the chamber via the inlet and outlet, (b) an annular seat in the chamber, the chamber containing an upstream flow zone $R_1$ between the inlet and the seat, and a downstream flow zone $R_2$ between the seat and the outlet, (c) and a diaphragm at the upstream side of the seat and extending crosswise thereof and crosswise of at least a portion of the zone $R_1$, the diaphragm carried for movement toward the seat when the vacuum level in $R_1$ rises to a predetermined level, to reduce or block fluid flow through the chamber, the diaphragm movable away from the seat when the vacuum level in $R_1$ falls below a predetermined level.

As will be seen, the upstream flow zone typically extends about the seat, and the diaphragm extends at one side of the upstream flow zone. Also, the chamber has an end wall and a generally annular side wall bounding the upstream flow zone, the diaphragm typically defining an opposite end wall for the chamber. Further, the downstream flow zone may define a 90° bend within the chamber.

Another object includes the provision of a chamber having a control port communicating between the described flow zone and the exterior of the device, that port adapted to be manually controlled by the user.

Another object includes the provision of a cap on the chamber protectively covering the diaphragm, the latter typically peripherally carried by the chamber proximate its side wall. A vent port may be provided through the cover to communicate the opposite side wall of the diaphragm with the exterior.

These and other objects and advantages of the invention, as well as the details of an illustrative embodiment, will be more fully understood from the following specification and drawings, in which:

DRAWING DESCRIPTION

FIG. 1 is a bottom plan view of apparatus embodying the invention;

FIG. 2 is a section taken on lines 2—2 of FIG. 1;

FIG. 3 is a perspective view of a chamber from which the diaphragm has been removed, to show interior construction; and FIG. 4 is a view like FIG. 2 showing a modification.

DETAILED DESCRIPTION

As shown in the drawings, a chamber 10 typically has a side wall 11 which may be cylindrical, a bottom wall 12, and a cap or cover 13. The latter has a skirt 13a to interfit side wall 11, and a top horizontal wall 13b. The chamber has an inlet as provided by stub tubing 14, at which a suction level or levels $V_x$ is or are to be maintained or monitored. The chamber also has an outlet, as may be provided by stub tubing 15, to which vacuum level $V_2$ is applied and wherein $V_x < V_2$, fluid being sucked through the chamber via the inlet and outlet.

An annular seat 16 is provided in the chamber, the chamber containing an upstream flow zone $R_1$ between the inlet and seat, and a downstream flow zone $R_2$ between the seat and outlet. A diaphragm 17 is provided at the upstream side of the seat and extends crosswise thereof and also crosswise of at least a portion of zone $R_1$. The diaphragm is carried for longitudinal movement toward the seat when the vacuum level in $R_1$ rises to a predetermined level to reduce or block fluid flow through the chamber. Conversely, the diaphragm is movable away from the seat when the vacuum level in $R_1$ falls below a predetermined level. Note in particular that such vacuum is applied to the annular portion 17a of the diaphragm which extends over $R_1$, that portion being thinner and more flexible than the thicker disc base portion 17b of the diaphragm that extends over the seat and over the mouth 18 of the 90° tubular bend 19 that is provided within the chamber and projects toward the diaphragm portion 17b. Thicker portion 17b extends diaphragm life considering that it impacts seat 16 as the diaphragm rapidly moves back and forth.

The diaphragm may have a peripheral skirt 17d that extends about the laterally facing wall of the chamber and is held in retained position between skirt 13a of the cap or cover and wall 11.

A suctioning device is indicated at 20 as connected with the inlet 14. It may for example be used for suctioning blood or other body fluid a referred to above. The outlet duct 15 may be plugged into an orifice 21 provided, as at the wall of a hospital room, to provide suction, at a level higher than the level to be provided at the suctioning device 20. Accordingly, the apparatus shown in the drawings serves to regulate the suction applied at 20.

The invention works in the following manner. In a flow-through system, the fluid will be sucked through the inlet port into the housing and out the outlet port. If the catheter that is connected to the inlet port should become occluded, then the vacuum level in the inlet chamber will rise rapidly to match the value of the vacuum source (say 700 mm Hg). But before the inlet and outlet vacuums equalize, the diaphragm will be pulled downward to shut off the central orifice 18 in the housing. The diaphragm's upper side is at atmospheric pressure; its lower side has applied vacuum level equal to the value at the inlet 14. The wall thickness and resiliency of the diaphragm determine the differential pressure needed to move the diaphragm and shut off the central orifice. With proper design of the diaphragm, this can be set at say 120 mm Hg.

As soon as the inlet chamber vacuum reaches 120 mm, the diaphragm shuts off. If the inlet chamber pressure increases because the catheter is no longer occluded, the diaphragm will unseat from the orifice and let the fluid flow through.

Experiments with the partially occluded catheter have shown that the diaphragm closes and opens, several times a second to regulate the vacuum. This vibration of the diaphragm produces a whistling sound that is quite loud and annoying. To eliminate this sound, a cover is placed over the diaphragm to dampen the vibration and minimize noise. The cover also protects the diaphragm from physical damage. The cover has a vent hole 50 that permits atmospheric pressure to be exerted on the top side of the diaphragm.

In the embodiment of FIG. 4, the construction is the same as described above except that a control port 22 is provided through the bottom wall 12. Port 22 may be located in a stub tubing 23 which also projects into the chamber at 23a and communicates with the zone $R_1$ and also with the exterior 24. The user may apply his finger or thumb over the port to activate the regulator device. Otherwise, the system is open to the atmosphere and no suction is available in the catheter or suctioning device 20 referred to above.

It will be understood that the cap 13 may advantageously incorporate cap structure extending in such proximity to the diaphragm 17 as to dampen diaphragm resonance (fluttering). In the example, that structure takes the form of a projection or bottom 40 integral with the cap wall 13b, and extending toward the diaphragm to deflect a medial portion thereof toward the seat 16 when the diaphragm takes or occupies its FIG. 2 position furthest from that seat.

Further, in the interests of simplicity, a peripheral annular bead 52, which may be integral with the diaphragm, projects radially inwardly and retains the diaphragm skirt 17d to the chamber side wall 11. Note annular recess 11a in wall 11 receiving that bead.

FIG. 2 shows stub tubing 15 provided with a series of external stepped connection shoulders 15a, for attachment of tubing. Also shown is a catheter 54 attached to stub tubing.

Unique advantages of the device include:
1. accurate vacuum limiting,
2. no moving parts except diaphragm,
3. compact, low cost design,
4. pre-set vacuum level determined by diaphragm shape; no adjustment need be made by user;
5. device operates in any orientation,
6. cover eliminates resonance and whistling of diaphragm.

The chamber may consist of molded plastic material, and the diaphragm may consist of elastomeric material.

We claim:

1. In a device for limiting the applied vacuum in a fluid suctioning system, the combination comprising
  (a) a chamber having an inlet at which a suction level or levels $V_x$ is or are to be maintained, and an outlet to which vacuum level $V_2$ is applied, wherein $V_x < V_2$, fluid being sucked through said chamber via said inlet and outlet,
  (b) an annular seat in said chamber, the chamber containing an upstream flow zone $R_1$ between said inlet and said seat, and a downstream flow zone $R_2$ between said seat and said outlet, the seat facing longitudinally,
  (c) and a diaphragm at the upstream side of the seat and extending crosswise thereof and crosswise of at least a portion of said zone $R_1$, the diaphragm having a top wall carried for longitudinal movement toward the seat when the vacuum level in $R_1$ rises to a predetermined level, to reduce or block fluid flow through the chamber, the diaphragm top wall movable away from the seat when the vacuum level in $R_1$ falls below a predetermined level,
  (d) the chamber having an outer wall that faces laterally and extends about said seat,
  (e) said diaphragm consisting of elastomeric material and having a peripheral skirt which extends in a position proximate said outer wall that faces laterally, the diaphragm skirt retained in said position for positioning said diaphragm top wall for said movement toward and away from the seat.
  (f) the diaphragm top wall substantially everywhere deflected toward the seat by the outer wall when the diaphragm top wall extends furthest from the seat.

2. The combination of claim 1 wherein the upstream flow zone extends about the seat, and the diaphragm extends at one side of the upstream flow zone.

3. The combination of claim 2 wherein the chamber has an end wall, and a generally annular side wall bounding the upstream flow zone, said diaphragm defining an opposite end wall for said chamber.

4. The combination of claim 2 wherein said downstream flow zone $R_2$ defines a 90° bend, within the chamber.

5. The combination of claim 1 including a relatively high vacuum source connected with said outlet.

6. The combination of claim 1 including a suctioning device connected with said inlet.

7. The combination of claim 5 including a suctioning device connected with said inlet.

8. The combination of claim 3 wherein said diaphragm is peripherally carried by said chamber, proximate said side wall.

9. The combination of claim 1 wherein said chamber also has a control port communicating between said zone $R_1$, and the exterior of said device, said port adapted to be manually controlled by a user.

10. The combination of claim 1 including a cap on said chamber protectively covering the diaphragm.

11. The combination of claim 10 including a vent port through said cover, to communicate that side of the diaphragm facing away from $R_1$ with the exterior.

12. The combination of claim 1 wherein the diaphragm top wall is thickened at a region facing the seat, the diaphragm shaped to regulate the vacuum to about 160 mm Hg when the suction applied to the outlet part is about 750 mm Hg.

13. The combination of claim 1 wherein said outer wall comprises cap structure on said chamber and extending in such proximity to the side of the diaphragm opposite the seat as to dampen diaphragm resonance said cap structure having a skirt which retains the diaphragm skirt to said chamber outer wall.

14. The combination of claim 13 wherein said cap structure includes a projection extending toward and engaging the diaphragm top wall to deflect a medial portion of the diaphragm top wall toward the seat when the diaphragm top wall extends furthest from the seat.

15. The combination of claim 3 wherein the diaphragm skirt has a peripheral inwardly facing bead that retains the diaphragm skirt to said chamber generally annular side wall.

16. The combination of claim 1 including an elongated, tubular fitting integral with said chamber to communicate with said outlet, said fitting defining a series of external stepped connection shoulders.

17. The combination of claim 1 including a catheter integral with said device and communication with said inlet.

* * * * *